(12) United States Patent
Chung et al.

(10) Patent No.: US 9,133,246 B2
(45) Date of Patent: Sep. 15, 2015

(54) SURFACE-ACTIVE COLLAGEN MEMBRANE BY PEPTIDE (75) Inventors: Chong-Pyoung Chung, Seoul (KR); Yoon-Jeong Park, Seoul (KR); Jue-Yeon Lee, Gyeonggi-do (KR); In Kyong Shim, Seoul (KR); Hyun Jung Park, Seoul (KR)

(73) Assignee: NANO INTELLIGENT BIOMEDICAL ENGINEERING CORPORATION CO, LTD., Seoul (KR)

( * ) Notice: Subject to any disclaimer, the term of this patent is extended or adjusted under 35 U.S.C. 154(b) by 0 days.

(21) Appl. No.: 14/112,929

(22) PCT Filed: Dec. 16, 2011

(86) PCT No.: PCT/KR2011/009708
§ 371 (c)(1),
(2), (4) Date: Nov. 25, 2013

(87) PCT Pub. No.: WO2012/144719
PCT Pub. Date: Oct. 26, 2012

(65) Prior Publication Data
US 2014/0187743 A1 Jul. 3, 2014

(30) Foreign Application Priority Data
Apr. 22, 2011 (KR) ........................ 10-2011-0037840

(51) Int. Cl.
| | |
|---|---|
| A61K 38/00 | (2006.01) |
| C07K 14/78 | (2006.01) |
| C07K 14/00 | (2006.01) |
| A61L 27/24 | (2006.01) |
| A61L 27/54 | (2006.01) |
| A61L 27/60 | (2006.01) |
| C12N 15/62 | (2006.01) |
| C07K 14/49 | (2006.01) |
| C07K 14/51 | (2006.01) |
| C07K 14/47 | (2006.01) |
| C07K 14/485 | (2006.01) |

(52) U.S. Cl.
CPC .............. *C07K 14/001* (2013.01); *A61L 27/24* (2013.01); *A61L 27/54* (2013.01); *A61L 27/60* (2013.01); *C07K 14/4723* (2013.01); *C07K 14/485* (2013.01); *C07K 14/49* (2013.01); *C07K 14/51* (2013.01); *C07K 14/78* (2013.01); *C12N 15/62* (2013.01); *A61K 38/00* (2013.01); *A61L 2300/252* (2013.01); *A61L 2300/404* (2013.01); *A61L 2300/80* (2013.01); *A61L 2430/02* (2013.01); *C07K 2319/00* (2013.01)

(58) Field of Classification Search
CPC ............. A61K 38/00; A61L 2300/252; A61L 2300/404; A61L 2300/80; A61L 2430/02; A61L 27/24; A61L 27/54; A61L 27/60; C07K 14/001; C07K 14/4723; C07K 14/78; C07K 2319/00
USPC ................................. 530/324, 356
See application file for complete search history.

(56) References Cited

U.S. PATENT DOCUMENTS

| | | | |
|---|---|---|---|
| 6,809,181 B2 | 10/2004 | McCray, Jr. et al. | |
| 7,488,792 B2 | 2/2009 | Ruoslahti et al. | |
| 2005/0014932 A1* | 1/2005 | Imboden et al. | ............... 530/350 |

FOREIGN PATENT DOCUMENTS

| | | |
|---|---|---|
| KR | 2003-0002224 A | 1/2003 |
| KR | 10-0564366 A | 4/2006 |

OTHER PUBLICATIONS

Abd-Elgaliel WR, Tung C-H, "Exploring the Structural Requirements of Collagen-Binding Peptides," PeptideScience, Published online Nov. 22, 2012, 100(2):167-173.*
Lee J-Y, Choo J-E, Choi, Y-S, Park J-B, Min D-S, Lee S-J, Rhyu HK, Ho I-H, Chung C-P, Park Y-J, "Assembly of collagen-binding peptide with collagen as a bioactive scaffold for osteogenesis in itro and in vivo," Biomaterials, 2007, 28:4257-4267.*
Kaigler, D., et al., "Platelet-Derived Growth Factor Applications in Periodontal and Peri-Implant Bone Regeneration", "Expert Opin Biol Ther", Feb. 3, 2011, pp. 375385, vol. 11, No. 3.
Sun, W., et al., "Collagen membranes loaded with collagen-binding human PDGF-BB accelerate wound healing in a rabbit dermal ischemic ulcer model", "Growth Factors", Oct. 2007, pp. 309318, vol. 25, No. 5.

* cited by examiner

*Primary Examiner* — Julie Ha
(74) *Attorney, Agent, or Firm* — Hultquist, PLLC; Steven J. Hultquist (57) ABSTRACT

A collagen membrane having fusion protein bound thereto is described, in which the fusion protein includes collagen binding peptide and antibacterial peptide. The collagen membrane is usefully employed in vivo to promote cell migration, proliferation, and differentiation associated with bone tissue regeneration, for bone induction and regeneration. The fusion protein may also be applied to other collagenic graft materials, for use as a biomaterial for regenerating other tissues such as the skin.

3 Claims, 6 Drawing Sheets

Surface

Section

SEQUENCE LISTING

```
<160> NUMBER OF SEQ ID NOS: 29

<210> SEQ ID NO 1
<211> LENGTH: 19
<212> TYPE: PRT
<213> ORGANISM: Artificial
<220> FEATURE:
<223> OTHER INFORMATION: Collagen Binding Peptide

<400> SEQUENCE: 1

Gly Leu Arg Ser Lys Ser Lys Lys Phe Arg Arg Pro Asp Ile Gln Tyr
1               5                   10                  15

Pro Asp Ala

<210> SEQ ID NO 2
<211> LENGTH: 17
<212> TYPE: PRT
<213> ORGANISM: Artificial
<220> FEATURE:
<223> OTHER INFORMATION: BMP-2

<400> SEQUENCE: 2

Val Ala Gly Thr Arg Cys Leu Leu Ala Leu Leu Leu Pro Gln Val Leu
1               5                   10                  15

Leu

<210> SEQ ID NO 3
<211> LENGTH: 17
<212> TYPE: PRT
<213> ORGANISM: Artificial
<220> FEATURE:
<223> OTHER INFORMATION: BMP-4

<400> SEQUENCE: 3

Ile Pro Gly Asn Arg Met Leu Met Val Val Leu Leu Cys Gln Val Leu
1               5                   10                  15

Leu

<210> SEQ ID NO 4
<211> LENGTH: 17
<212> TYPE: PRT
<213> ORGANISM: Artificial
<220> FEATURE:
<223> OTHER INFORMATION: BMP-6

<400> SEQUENCE: 4

Pro Gly Leu Gly Arg Arg Ala Gln Trp Leu Cys Trp Trp Trp Gly Leu
1               5                   10                  15

Leu

<210> SEQ ID NO 5
<211> LENGTH: 19
<212> TYPE: PRT
```

```
<213> ORGANISM: Artificial
<220> FEATURE:
<223> OTHER INFORMATION: BMP-2

<400> SEQUENCE: 5

Val Leu Leu Gly Gly Ala Ala Gly Leu Val Pro Glu Leu Gly Arg Arg
1               5                   10                  15

Lys Phe Ala

<210> SEQ ID NO 6
<211> LENGTH: 25
<212> TYPE: PRT
<213> ORGANISM: Artificial
<220> FEATURE:
<223> OTHER INFORMATION: BMP-2

<400> SEQUENCE: 6

Asp Glu Val Leu Ser Glu Phe Glu Leu Arg Leu Leu Ser Met Phe Gly
1               5                   10                  15

Leu Lys Gln Arg Pro Thr Pro Ser Arg
            20                  25

<210> SEQ ID NO 7
<211> LENGTH: 20
<212> TYPE: PRT
<213> ORGANISM: Artificial
<220> FEATURE:
<223> OTHER INFORMATION: BMP-2

<400> SEQUENCE: 7

Ala Val Val Pro Pro Tyr Met Leu Asp Leu Tyr Arg Arg His Ser Gly
1               5                   10                  15

Gln Pro Gly Ser
            20

<210> SEQ ID NO 8
<211> LENGTH: 18
<212> TYPE: PRT
<213> ORGANISM: Artificial
<220> FEATURE:
<223> OTHER INFORMATION: BMP-2

<400> SEQUENCE: 8

Gly Gln Pro Gly Ser Pro Ala Pro Asp His Arg Leu Glu Arg Ala Ala
1               5                   10                  15

Ser Arg

<210> SEQ ID NO 9
<211> LENGTH: 19
<212> TYPE: PRT
<213> ORGANISM: Artificial
<220> FEATURE:
<223> OTHER INFORMATION: BMP-2

<400> SEQUENCE: 9

Arg His Pro Leu Tyr Val Asp Phe Ser Asp Val Gly Trp Asn Asp Trp
1               5                   10                  15

Ile Val Ala

<210> SEQ ID NO 10
<211> LENGTH: 19
<212> TYPE: PRT
<213> ORGANISM: Artificial
<220> FEATURE:
```

```
<223> OTHER INFORMATION: BMP-2

<400> SEQUENCE: 10

Asp His Leu Asn Ser Thr Asn His Ala Ile Val Gln Thr Leu Val Asn
1               5                   10                  15

Ser Val Asn

<210> SEQ ID NO 11
<211> LENGTH: 27
<212> TYPE: PRT
<213> ORGANISM: Artificial
<220> FEATURE:
<223> OTHER INFORMATION: BMP-2

<400> SEQUENCE: 11

Ser Met Leu Tyr Leu Asp Glu Asn Glu Lys Val Val Leu Lys Asn Tyr
1               5                   10                  15

Gln Asp Met Val Val Glu Gly Cys Gly Cys Arg
            20                  25

<210> SEQ ID NO 12
<211> LENGTH: 20
<212> TYPE: PRT
<213> ORGANISM: Artificial
<220> FEATURE:
<223> OTHER INFORMATION: BMP-4

<400> SEQUENCE: 12

Ser Lys Ser Ala Val Ile Pro Asp Tyr Met Arg Asp Leu Tyr Arg Leu
1               5                   10                  15

Gln Ser Gly Glu
            20

<210> SEQ ID NO 13
<211> LENGTH: 21
<212> TYPE: PRT
<213> ORGANISM: Artificial
<220> FEATURE:
<223> OTHER INFORMATION: BMP-4

<400> SEQUENCE: 13

Ser Pro Lys His His Ser Gln Arg Ala Arg Lys Lys Asn Lys Asn Cys
1               5                   10                  15

Arg Arg His Ser Leu
            20

<210> SEQ ID NO 14
<211> LENGTH: 20
<212> TYPE: PRT
<213> ORGANISM: Artificial
<220> FEATURE:
<223> OTHER INFORMATION: BMP-4

<400> SEQUENCE: 14

Leu Val Asn Ser Val Asn Ser Ser Ile Pro Lys Ala Cys Cys Val Pro
1               5                   10                  15

Thr Glu Leu Ser
            20

<210> SEQ ID NO 15
<211> LENGTH: 11
<212> TYPE: PRT
<213> ORGANISM: Artificial
<220> FEATURE:
```

```
<223> OTHER INFORMATION: BMP-4

<400> SEQUENCE: 15

Ser Met Leu Tyr Leu Asp Glu Tyr Asp Lys Val
1               5                   10

<210> SEQ ID NO 16
<211> LENGTH: 19
<212> TYPE: PRT
<213> ORGANISM: Artificial
<220> FEATURE:
<223> OTHER INFORMATION: BMP-6

<400> SEQUENCE: 16

Arg Pro Arg Pro Leu His Gly Leu Gln Gln Pro Gln Pro Pro Ala Leu
1               5                   10                  15

Arg Gln Gln

<210> SEQ ID NO 17
<211> LENGTH: 12
<212> TYPE: PRT
<213> ORGANISM: Artificial
<220> FEATURE:
<223> OTHER INFORMATION: BMP-6

<400> SEQUENCE: 17

Glu Leu Lys Thr Ala Cys Arg Lys His Glu Leu Tyr
1               5                   10

<210> SEQ ID NO 18
<211> LENGTH: 19
<212> TYPE: PRT
<213> ORGANISM: Artificial
<220> FEATURE:
<223> OTHER INFORMATION: BMP-6

<400> SEQUENCE: 18

Tyr Val Pro Lys Pro Cys Cys Ala Pro Thr Lys Leu Asn Ala Ile Ser
1               5                   10                  15

Val Leu Tyr

<210> SEQ ID NO 19
<211> LENGTH: 24
<212> TYPE: PRT
<213> ORGANISM: Artificial
<220> FEATURE:
<223> OTHER INFORMATION: BMP-6

<400> SEQUENCE: 19

Ser Val Leu Tyr Phe Asp Asp Asn Ser Asn Val Ile Leu Lys Lys Tyr
1               5                   10                  15

Arg Asn Met Val Val Arg Ala Cys
            20

<210> SEQ ID NO 20
<211> LENGTH: 20
<212> TYPE: PRT
<213> ORGANISM: Artificial
<220> FEATURE:
<223> OTHER INFORMATION: BMP-7

<400> SEQUENCE: 20

Pro Gly Gly Gln Gly Phe Ser Tyr Pro Tyr Lys Ala Val Phe Ser Thr
1               5                   10                  15
```

```
Gln Gly Pro Pro
            20

<210> SEQ ID NO 21
<211> LENGTH: 21
<212> TYPE: PRT
<213> ORGANISM: Artificial
<220> FEATURE:
<223> OTHER INFORMATION: BMP-7

<400> SEQUENCE: 21

Glu Asn Ser Ser Ser Asp Gln Arg Gln Ala Cys Lys Lys His Glu Leu
1               5                   10                  15

Tyr Val Ser Phe Arg
            20

<210> SEQ ID NO 22
<211> LENGTH: 10
<212> TYPE: PRT
<213> ORGANISM: Artificial
<220> FEATURE:
<223> OTHER INFORMATION: BMP-7

<400> SEQUENCE: 22

Gln Leu Asn Ala Ile Ser Val Leu Tyr Phe
1               5                   10

<210> SEQ ID NO 23
<211> LENGTH: 19
<212> TYPE: PRT
<213> ORGANISM: Artificial
<220> FEATURE:
<223> OTHER INFORMATION: BMP-7

<400> SEQUENCE: 23

Ser Val Leu Tyr Phe Asp Asp Ser Ser Asn Val Ile Leu Lys Lys Tyr
1               5                   10                  15

Arg Asn Met

<210> SEQ ID NO 24
<211> LENGTH: 38
<212> TYPE: PRT
<213> ORGANISM: Artificial
<220> FEATURE:
<223> OTHER INFORMATION: Collagen Binding Peptide

<400> SEQUENCE: 24

Gly Leu Arg Ser Lys Ser Lys Lys Phe Arg Arg Pro Asp Ile Gln Tyr
1               5                   10                  15

Pro Asp Ala Arg His Pro Leu Tyr Val Asp Phe Ser Asp Val Gly Trp
            20                  25                  30

Asn Asp Trp Ile Val Ala
                35

<210> SEQ ID NO 25
<211> LENGTH: 22
<212> TYPE: PRT
<213> ORGANISM: Artificial
<220> FEATURE:
<223> OTHER INFORMATION: hBD2-2

<400> SEQUENCE: 25

Cys Pro Arg Arg Tyr Lys Gln Ile Gly Thr Cys Gly Leu Pro Gly Thr
1               5                   10                  15
```

```
Lys Cys Cys Lys Lys Pro
            20

<210> SEQ ID NO 26
<211> LENGTH: 15
<212> TYPE: PRT
<213> ORGANISM: Artificial
<220> FEATURE:
<223> OTHER INFORMATION: hBD3-3

<400> SEQUENCE: 26

Gly Lys Cys Ser Thr Arg Gly Arg Lys Cys Cys Arg Arg Lys Lys
1               5                   10                  15

<210> SEQ ID NO 27
<211> LENGTH: 18
<212> TYPE: PRT
<213> ORGANISM: Artificial
<220> FEATURE:
<223> OTHER INFORMATION: PDGF3

<400> SEQUENCE: 27

Arg Lys Ile Glu Ile Val Arg Lys Lys Pro Ile Phe Lys Lys Ala Thr
1               5                   10                  15

Val Thr

<210> SEQ ID NO 28
<211> LENGTH: 22
<212> TYPE: PRT
<213> ORGANISM: Artificial
<220> FEATURE:
<223> OTHER INFORMATION: HB-EGF

<400> SEQUENCE: 28

Cys Lys Arg Lys Lys Lys Gly Lys Gly Leu Gly Lys Lys Arg Asp Pro
1               5                   10                  15

Cys Leu Arg Lys Tyr Lys
            20

<210> SEQ ID NO 29
<211> LENGTH: 34
<212> TYPE: PRT
<213> ORGANISM: Artificial
<220> FEATURE:
<223> OTHER INFORMATION: Collagen Binding Peptide

<400> SEQUENCE: 29

Gly Leu Arg Ser Lys Ser Lys Lys Phe Arg Arg Pro Asp Ile Gln Tyr
1               5                   10                  15

Pro Asp Ala Gly Lys Cys Ser Thr Arg Gly Arg Lys Cys Cys Arg Arg
            20                  25                  30

Lys Lys
```

SURFACE-ACTIVE COLLAGEN MEMBRANE BY PEPTIDE

CROSS-REFERENCE TO RELATED APPLICATIONS

This application is a U.S. national phase under the provisions of 35 U.S.C. §371 of International Patent Application No. PCT/KR11/09708 filed Dec. 16, 2011, which in turn claims the priority of Korean Patent Application No. 10-2011-0037840 filed Apr. 22, 2011. The disclosures of such international patent application and Korean priority patent application are hereby incorporated herein by reference in their respective entireties, for all purposes.

TECHNICAL FIELD

The present invention relates to a membrane having bound thereto an antibacterial peptide that binds to collagen, and more particularly to a collagen membrane comprising a fusion peptide of a collagen-binding peptide and an antibacterial peptide, fixed to the collagen surface.

BACKGROUND ART

Methods for regenerating alveolar bone damaged by periodontal diseases include a method in which the bone defect is filled with an autograft. Another method uses either a human or animal bone, the immunogenicity of which was removed, as an artificial bone replacement material, or a commercially available hydroxyapatite.

In recent years, there has been an active attempt to introduce an artificial membrane into damaged periodontal tissue in order to promote the healing of the damaged tissue, induce the restoration of complete periodontal tissue, improve the result of bone grafting and induce the production of new periodontal bone. The membrane that is used in this technology isolates and blocks the damaged site from the surrounding connective tissue to produce new periodontal bone and periodontal ligament tissue so that the regeneration of periodontal tissue can smoothly occur. In other words, the damaged site is blocked from the surrounding environment by the membrane so that gingival fibroblasts cannot invade the damaged site, and cells in the tissue, which has the ability to regenerate bone and a periodontal ligament, can regenerate new periodontal tissue without interference.

In addition, because bone damage caused by various diseases or trauma has an important influence on human movement, a treatment is required, which can maintain the continuity of the skeletal system and mechanically support the body. Currently, bone regeneration or bone replacement treatments are frequently being performed, but have many problems.

Previously, non-degradable materials such as polytetrafluoroethylene, cellulose acetate, silicone rubber and polyurethane were used as the membrane. However, a membrane made of a non-degradable material has low biocompatibility, and for this reason, secondary surgery is required to remove the membrane after production of periodontal bone, and in this procedure, unnecessary inflammation or tissue necrosis can occur.

Recently, studies on the use of biodegradable polymers such as aliphatic polyester or collagen have been reported. It has also been reported that the use of a biodegradable membrane eliminates the need for secondary surgery for removing the membrane and has no significant difference from the use of a membrane made of a non-degradable material in tissue regeneration. However, in the case of a membrane made of aliphatic polyester, acidic degradation products can cause an inflammatory reaction in the grafted site. Thus, there was a report on the use of a membrane made of collagen, which forms a great part of bone tissue protein, in clinical trials.

In the prior art, Korean Patent Laid-Open Publication No. 2003-002224 discloses a membrane for inducing tissue regeneration, which is prepared from the natural polymer chitosan and a synthetic biodegradable polymer. Herein, the membrane is prepared by applying a biodegradable polymer solution to a nonwoven fabric made of chitosan to form a polymer film, and then laminating the nonwoven fabric made of chitosan on the polymer film, and thus there is a shortcoming in that the preparation process is complex. In addition, Korean Registration No. 0564366 discloses a membrane for tissue regeneration, which comprises a nonwoven nanofiber fabric, has a specific strength, biocompatibility and biodegradability, includes micropores whose pore size can be easily controlled, and can be prepared from a mixture of a natural polymer and a synthetic polymer by a simple process. However, such a conventional membrane for tissue regeneration has a drawback in that, because a tissue growth factor is physically mixed with this polymer membrane or scaffold, it is immediately released after being applied, making it difficult to maintain the effective concentration thereof during a treatment period.

In addition, there was a study on introducing tissue growth factors or extracellular matrix-derived substances into a membrane in order to improve the tissue regeneration ability of the membrane. Because these growth factors and substances are proteins, they should maintain their three-dimensional structure in order to maintain their activity. However, there is a shortcoming in that most of these growth factors and extracellular matrix-derived substances are susceptible to temperature, and thus are likely to be unstable in vivo.

Thus, in order to obtain a desired therapeutic effect, tissue growth factors and extracellular matrix-derived substances should be administered at high doses, but in this case, side effects can occur. In order to overcome this problem, an attempt was made to introduce tissue growth factors inside or the surface of a membrane. However, if a tissue growth factor is physically adsorbed onto a membrane, the bonding thereof cannot be maintained for a long period of time, whereas if a tissue growth factor is covalently bonded to a membrane, the bonding thereof can be stably maintained for a long period of time using a crosslinking agent. However, in this case, there is a problem in that the crosslinking agent can result in the deformation of the three-dimensional structure of the tissue growth factor, resulting in a decrease in the activity of the tissue growth factor.

Accordingly, the present inventors have made extensive efforts to prepare a collagen membrane having antibacterial activity on the surface thereof, and as a result, have found that, when a fusion peptide consisting of an antibacterial peptide linked to a peptide having the ability to bind to collagen is bound to a collagen membrane, it can impart surface antibacterial activity to the membrane, thereby completing the present invention.

DISCLOSURE OF INVENTION

Technical Problem

It is an object of the present invention to provide a collagen membrane, which has bound thereto a fusion peptide consisting of an antibacterial peptide linked to a peptide having the ability to bind to collagen, and thus has surface antibacterial activity.

Technical Solution

To achieve the above object, the present invention provides a fusion peptide having collagen-binding ability and antibacterial activity, the fusion peptide comprising a collagen-binding peptide linked to a peptide having an amino acid sequence selected from the group consisting of amino acid sequences of SEQ ID NO: 25 to SEQ ID NO: 28. The present invention also provides a collagen membrane having antibacterial activity, the collagen membrane comprising said fusion peptide fixed to the surface thereof.

BRIEF DESCRIPTION OF THE DRAWINGS

FIG. 3A shows a collagen membrane having no peptide bound thereto, and FIG. 3B shows a collagen membrane having bound thereto a peptide of SEQ ID NO: 24 labeled with FITC.

FIG. 5A shows a membrane having bound thereto a peptide of SEQ ID NO: 1; FIG. 5B shows a membrane having bound thereto a peptide of SEQ ID NO: 9; and FIG. 5C shows a membrane having bound thereto a peptide of SEQ ID NO: 24.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

In one aspect, the present invention is directed to a fusion peptide having collagen-binding ability and antibacterial activity, the fusion peptide comprising a collagen-binding peptide linked to a peptide having an amino acid sequence selected from the group consisting of amino acid sequences of SEQ ID NO: 25 to SEQ ID NO: 28.

The collagen-binding peptide that is used in the present invention may be any peptide having the ability to bind to collagen. In an example of the present invention, a peptide having an amino acid sequence set forth in SEQ ID NO: 1 was used as the collagen-binding peptide, but is not limited thereto.

SEQ ID NO: 1: GLRSKSKKFRRPDIQYPDA

The antibacterial peptide of the present invention may be selected from the group consisting of peptides derived from human beta-defensin-2 (hBD-2: SEQ ID NO: 25), human beta-defensin-3 (hBD-3: SEQ ID NO: 26), human platelet derived growth factor-B (PDGF-B: SEQ ID NO: 27) and heparin-binding epidermal growth factor (HB-EGF: SEQ ID NO: 28).

The amino acid sequences of SEQ ID NOS: 25 to 28 are as follows:

SEQ ID NO: 25(BD2-2): CPRRYKQIGTCGLPGTKCCKKP

SEQ ID NO: 26(BD3-3): GKCSTRGRKCCRRKK

SEQ ID NO: 27(PDGF): RKIEIVRKKPIFKKATVT

SEQ ID NO: 28(HB-EGF): CKRKKKGKGLGKKRDPCLRKYK

In the present invention, the fusion peptide may have an amino acid sequence set forth in SEQ ID NO: 29.

In an example of the present invention, the collagen-binding peptide of SEQ ID NO: 1 was linked to the antibacterial peptide of SEQ ID NO: 26 to prepare the collagen-binding antibacterial peptide of SEQ ID NO: 29, and whether the prepared peptide stably binds to collagen to exhibit antibacterial activity was examined by measuring the inhibitory activity of the peptide against bacterial growth.

SEQ ID NO: 29:
GLRSKSKKFRRPDIQYPDAGKCSTRGRKCCRRKK

In another aspect, the present invention is directed to a collagen membrane having antibacterial activity, the collagen membrane comprising said fusion peptide fixed to the surface thereof.

The fusion peptide comprising the collagen-binding peptide according to the present invention can be fixed to collagen, and thus the retention time of the peptide in a local region can increase and the bone regenerating effect and antibacterial effect of the peptide can be long lasting, suggesting that it is suitable for regeneration of bone tissue and periodontal tissue.

In an example of the present invention, in order to prepare a fusion peptide for bone tissue regeneration that binds specifically to collagen, a collagen-binding peptide of SEQ ID NO: 1 and an antibacterial peptide of SEQ ID NO: 26 were synthesized, and an antibacterial fusion peptide (SEQ ID NO: 29) that binds specifically to collagen was prepared using the synthesized peptides in the same manner as described above.

In another example of the present invention, in order to examine the antibacterial activity of an antibacterial fusion peptide that binds specifically to collagen, a collagen membrane was prepared using each of the peptides of SEQ ID NO: 1, the peptide of SEQ ID NO: 26 and the peptide of SEQ ID NO: 29 in the same manner as described in Example 2. The prepared collagen membrane was washed in PBS for 1 hour and dried in air. To evaluate the antibacterial activity of the peptide, an antibacterial test was performed according to an agar diffusion method. Specifically, *E. coli* cells were cultured in TSB medium until the absorbance at 620 nm reached 1, and then the cells were harvested and used in the test. The harvested cells were diluted with PBS, and $10^5$-$10^7$ bacterial cells per ml were plated on a TSA plate and incubated at 37° C for 24 hours. On the plate having the incubated bacterial cells thereon, a collagen membrane having each of the peptides of SEQ ID NOS: 1, 26 and 29 bound thereto was placed and incubated for 3 days. Then, the inhibition diameter against the growth of the bacterial cells was measured. As a result, it could be seen that the collagen membrane having the peptide of SEQ ID NO: 1 bound thereto had no antibacterial activity before and after washing, and the collagen membrane having the peptide of SEQ ID NO: 26 bound thereto showed the highest antibacterial activity before washing, but the antibacterial activity thereof decreased by about 50% after washing. In addition, the collagen membrane having the peptide of SEQ ID NO: 29 bound thereto maintained its antibacterial activity after washing compared to before washing. This suggests that the fusion peptide of the collagen-binding peptide and the antibacterial peptide maintained its collagen-binding ability even after washing, and for this reason, the antibacterial activity thereof did not change.

In the present invention, the peptide that binds to collagen is the peptide of SEQ ID NO: 1 (GLRSKSKKFRRP-DIQYPDA) and is chemically added to the N-terminus of a peptide for bone tissue regeneration, thereby increasing the collagen-binding ability of the peptide so that the peptide can stably bind to a membrane or a graft material.

In the present invention, the peptide having the ability to regenerate bone tissue may be selected from an amino acid sequence consisting of amino acids 2-18 of each of the amino acid sequences of bone morphogenetic protein-2 (BMP-2: SEQ ID NO: 2), bone morphogenetic protein-4 (BMP-4: SEQ ID NO: 3) and bone morphogenetic protein-6 (BMP-6: SEQ ID NO: 4), an amino acid sequence (SEQ ID NO: 5) consisting of amino acids 16-34 of BMP-2, an amino acid sequence (SEQ ID NO: 6) consisting of amino acids 47-71 of BMP-2, an amino acid sequence (SEQ ID NO: 7) consisting of amino acids 73-92 of BMP-2, an amino acid sequence (SEQ ID NO: 8) consisting of amino acids 88-105 of BMP-2, an amino acid sequence (SEQ ID NO: 9) consisting of amino acids 298-316 of BMP-2, an amino acid sequence (SEQ ID NO: 10) consisting of amino acids 335-353 of BMP-2, an amino acid sequence (SEQ ID NO: 11) consisting of amino acids 370-396 of BMP-2, an amino acid sequence (SEQ ID NO: 12) consisting of amino acids 74-93 of BMP-4, an amino acid sequence (SEQ ID NO: 13) consisting of amino acids 293-313 of BMP-4, an amino acid sequence (SEQ ID NO: 14) consisting of amino acids 360-379 of BMP-4, an amino acid sequence (SEQ ID NO: 15) consisting of amino acids 382-402 of BMP-4, an amino acid sequence (SEQ ID NO: 16) consisting of amino acids 91-110 of BMP-6, an amino acid sequence (SEQ ID NO: 17) consisting of amino acids 407-418 of BMP-6, an amino acid sequence (SEQ ID NO: 18) consisting of amino acids 472-490 of BMP-6, an amino acid sequence (SEQ ID NO: 19) consisting of amino acids 487-510 of BMP-6, an amino acid sequence (SEQ ID NO: 20) consisting of amino acids 98-117 of BMP-7, an amino acid sequence (SEQ ID NO: 21) consisting of amino acids 320-340 of BMP-7, an amino acid sequence (SEQ ID NO: 22) consisting of amino acids 400-409 of BMP-7, and an amino acid sequence (SEQ ID NO: 23) consisting of amino acids 405-423 of BMP-7.

The amino acid sequences of SEQ ID NOS: 2 to 23 are as follows:

```
SEQ ID NO: 2:    VAGTRCLLA LLLPQVLL

SEQ ID NO: 3:    IPGNRMLMV VLLCQVLL

SEQ ID NO: 4:    PGLGRRAQW LCWWWGLL
```

-continued
```
SEQ ID NO: 5:    VLLGG AAGLVPELGR RKFA

SEQ ID NO: 6:    DEVL SEFELRLLSM FGLKQRPTPS R

SEQ ID NO: 7:    AVVPPYML DLYRRHSGQP GS

SEQ ID NO: 8:    GQP GSPAPDHRLE RAASR

SEQ ID NO: 9:    RHPLYVDFSDVGW NDWIVA

SEQ ID NO: 10:   DHLNST NHAIVQTLVN SVN

SEQ ID NO: 11:   S MLYLDENEKV VLKNYQDMVV EGCGCR

SEQ ID NO: 12:   SKSAVIP DYMRDLYRLQ SGE

SEQ ID NO: 13:   SPKHHSQR ARKKNKNCRR HSL

SEQ ID NO: 14:   L VNSVNSSIPK ACCVPTELS

SEQ ID NO: 15:   SMLYLDEYD KV

SEQ ID NO: 16:   RPRPLHGLQ QPQPPALRQQ

SEQ ID NO: 17:   ELKT ACRKHELY

SEQ ID NO: 18:   YVPKPCCAPTKLNAISVLY

SEQ ID NO: 19:   SVLY FDDNSNVILK KYRNMVVRAC

SEQ ID NO: 20:   PGG QGFSYPYKAV FSTQGPP

SEQ ID NO: 21:   ENSSSDQRQAC KKHELYVSFR

SEQ ID NO: 22:   Q LNAISVLYF

SEQ ID NO: 23:   SVLYFD DSSNVILKKY RNM
```

In another example of the present invention, the collagen-binding peptide of SEQ ID NO: 1 was linked to the peptide of SEQ ID NO: 9 that has the ability to regenerate bone tissue, thereby preparing the peptide of SEQ ID NO: 24 that binds to collagen and has the ability to regenerate bone tissue. In addition, whether the prepared peptide stably binds to collagen was examined, and the membrane was transplanted into a bone defect in order to examine the ability to regenerate bone tissue.

In still another example of the present invention, a fusion peptide for bone tissue regeneration that binds specifically to collagen was synthesized by a Fmoc solid phase synthesis method using a peptide synthesizer so as to comprise the peptide of SEQ ID NO: 1 (GLRSKSKKFRRPDIQYPDA) that binds to collagen and the peptide of SEQ ID NO: 9 (RHPLYVDFSDVGWNDWIVA) that has the ability to regenerate bone tissue, sequentially from the N-terminus. Specifically, a Rink resin having the blocking group Fmoc-(9-Fluorenylmethoxycarbonyl) bound thereto was placed in a synthesizer and swollen with DMF, and then the Fmoc group was removed using 20% piperidine/DMF. Then, according to the sequence from the C-terminus, 0.5M amino acid solution (solvent: DMF), 1.0M DIPEA (solvent: DMF&NMP) and 0.5M HBTU (solvent: DMF) were introduced in the synthesizer and reacted under a nitrogen stream for 1-2 hours. Whenever the deprotection and coupling steps were ended, washing with DMF was carried out twice, and even after the coupling of the final amino acid, deprotection was carried out to remove the Fmoc group, thereby preparing a fusion peptide (SEQ ID NO: 24) for bone tissue regeneration that binds specifically to collagen.

```
SEQ ID NO: 24:
GLRSKSKKFRRPDIQYPDARHPLYVDFSDVGWNDWIVA
```

In still another example of the present invention, the synthesis of a fusion peptide for bone tissue regeneration that binds specifically to collagen was confirmed using the ninhydrin test. After the test and completion of the synthesis, the resin was dried with DCM, and then a TFA cleavage cocktail was added to the resin, and the mixture was shaken for 3 hours and filtered to separate the resin from a cocktail having the peptide dissolved therein. The filtered solution was removed using a rotary evaporator, and cold ether was added directly to the TFA cocktail solution having the peptide dissolved therein to crystallize the peptide into a solid which was then isolated by centrifugation. The synthesized peptide sequence was cleaved from the resin, washed, freeze-dried and then purified by liquid chromatography. The purified peptide was analyzed by MALDI to determine the molecular weight. In addition, to test the in vivo stability of the peptide, FITC (fluorescein isothiocyanate) was bound to the N-terminus of the peptide of SEQ ID NO: 24 using triethylamine, and the synthesis of the peptide was confirmed by MALDI-TOF.

In still another example of the present invention, in order to examine the collagen-binding ability of the fusion peptide that binds specifically to collagen, porcine sink-derived collagen was dissolved in 0.1M HCl at a concentration of 1%(w/v), the pH was neutralized, and the collagen solution was concentrated to 4% by evaporating the solvent. To prepare a membrane, the concentrated collagen solution was poured into a 60 cm diameter dish and mixed, and to prepare a three-dimensional scaffold, the collagen solution was poured onto a 24-well plate for cell culture and mixed. Next, 1% glutaraldehyde or 1% glyceraldehyde was added to crosslink the collagen solution, which was then washed with distilled water and freeze-dried. The resulting membrane having a size of 1×1 cm and a thickness of 250 μm was wet with 10 mg of the fusion peptide of SEQ ID NO: 24 in 100 μl of DW, washed with PBS and freeze-dried. The collagen membrane having the peptide bound thereto was added to PBS and subjected to a peptide release teat at 37° C. After 7 days, 10 ml of the elution solvent added was completely removed, after which 10 ml of a fresh elution solvent was added to the collagen membrane which was then eluted at 37° C. for 4 weeks. After completion of the elution, the membrane was collected and the peptide content thereof was measured. The elution test was performed for 4 weeks and the content of the peptide in the eluate was measured, and as a result, in Lot Nos. 1, 2 and 3, the peak of the peptide was not observed at the retention time of 13 minutes, but the peptide contents measured after completion of the elution were 9.2 mg, 9.43 mg and 9.68 mg, suggesting that the peptide bound to the membrane was released into the eluate and that the peptide was stably bound to the membrane.

In still another example of the present invention, in order to examine the in vivo stability of the fusion peptide that binds to collagen and has the ability to regenerate bone tissue, the peptide of SEQ ID NO: 24 labeled with FITC was bound to the collagen membrane which was then transplanted into a rabbit skull defect. At 4 weeks after the transplantation, the animal was sacrificed, and the membrane transplanted into the skull defect was observed with a confocal microscope. Before and at days 1, 3, 7, 14, 21 and 28 after the membrane bound to the peptide of SEQ ID NO: 24 labeled with FITC was transplanted into the rabbit skull defect, the blood was collected and whether the peptide was released into the systemic blood was measured using a fluorometer. As a result, it was shown that the peptide was well fixed to the surface of the membrane transplanted into the skull and did not spread to the surrounding tissue and that the RFI values did not differ from the value before transplantation, suggesting that the peptide included in the membrane was not released into the blood and the peptide was well fixed to the collagen membrane.

In still another example of the present invention, in order to examine the in vivo bone regeneration ability of the fusion peptide that binds to the collagen membrane and has the ability to regenerate bone tissue, each of the peptides of SEQ ID NOS: 1, 9 and 24 was bound to the collagen membrane, and then transplanted into the circular skull defect of rabbits, and the bone regeneration ability was examined. Specifically, a circular bone defect having a diameter of 8 mm was formed in the skull of anesthetized rabbits and covered with the collagen membrane, and the periosteum and the skin were doubly sutured. At 4 weeks after the transplantation, the animal was sacrificed, and the collected sample was fixed in a formalin solution. The tissue was embedded to prepare a sample having a thickness of 20 μm. The sample was stained with fuchsin and toluidine blue to prepare a nondemineralized sample. The prepared sample was observed with an optical microscope and photographed. The bone regeneration effect of the membrane comprising the fusion peptide that binds specifically to collagen and has the ability to regenerate bone tissue was examined, and as a result, the bone regeneration ability of the collagen membrane having the peptide of SEQ ID NO: 24 bound thereto was increased compared to that of the collagen membrane having the peptide of SEQ ID NO: 1 or 9 bound thereto suggesting that the fusion peptide stably bound to collagen has an increased ability to regenerate bone tissue, because it stably resides in the transplanted site.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Preparation of Fusion Peptide that Binds Specifically to Collagen and has the Ability to Regenerate Bone Tissue A fusion peptide, which binds specifically to collagen and has the ability to regenerate bone tissue, was synthesized sequentially from the N-terminal end by a Fmoc solid phase synthesis method using a peptide synthesizer so as to comprise the peptide of SEQ ID NO: 1 (GLRSKSKKFRRP-DIQYPDA) that binds to collagen and the peptide of SEQ ID NO: 9 (RHPLYVDFSDVGWNDWIVA) that has the ability to regenerate bone tissue. Specifically, 50 mg of a Rink resin (0.075 mmol/g, 100-200 mesh, 1% DVB crosslinking) having the blocking group Fmoc-(9-fluorenylmethoxycarbonyl) bound thereto was introduced in a synthesizer and swollen with DMF, and then the Fmoc group was removed using 20 ml of 20% piperidine/DMF solution. According to the sequence from the C-terminus, 5 ml of 0.5M amino acid solution (solvent: DMF), 5 ml of 1.0M DIPEA (solvent: DMF&NMP) and 5 ml of 0.5M HBTU (solvent: DMF) were introduced in the synthesizer and allowed to react under a nitrogen atmosphere for 1-2 hours. When the deprotection and coupling steps were ended, washing with DMF was carried out twice, and even after the final amino acid was coupled, deprotection was carried out to remove the Fmoc group, thereby preparing a fusion peptide (SEQ ID NO: 24) for bone tissue regeneration that binds specifically to collagen.

SEQ ID NO: 24:
GLRSKSKKFRRPDIQYPDARHPLYVDFSDVGWNDWIVA

The synthesis of the peptide was confirmed using the ninhydrin test. After the test and completion of the synthesis, the resin was dried with DCM, and then a TFA cleavage cocktail was added to the resin at a ratio of 20 ml per g of the resin, and the mixture was shaken for 3 hours and filtered to separate the resin from the cocktail having the peptide dissolved therein. The filtered solution was removed using a rotary evaporator, and then 1 l of cold ether was added directly to the TFA cocktail solution having the peptide dissolved therein to crystallize the peptide into a solid which was then isolated by centrifugation. Herein, the TFA cocktail was completely removed by washing several times with ether and centrifugation, and the peptide thus obtained was dissolved in distilled water and freeze-dried. The synthesized peptide sequence was cleaved from the resin, washed, freeze-dried, and then isolated and purified by liquid chromatography. The purified peptide was found to have a molecular weight of 4534 as measured by MALDI analysis.

In addition, in order to test the in vivo stability of the peptide, 0.3 g of FITC (fluorescein isothiocyanate) was bound to the N-terminus of the peptide of SEQ ID NO: 24 in 12 ml of a reaction solvent (pyridine: DMC: MC=12:7:5). The resulting peptide was found to have a molecular weight of 4934 as measured by MALDI-TOF.

Example 2

Examination of Collagen-Binding Ability of Fusion Peptide that Binds Specifically to Collagen and has the Ability to Regenerate Bone Tissue 1 g of porcine skin-derived collagen was dissolved in 100 ml of 0.1M HCl at a concentration of 1%(w/v), and then the pH of the collagen solution was neutralized, and the solvent was evaporated to the collagen solution to 4%.

Figure 1:
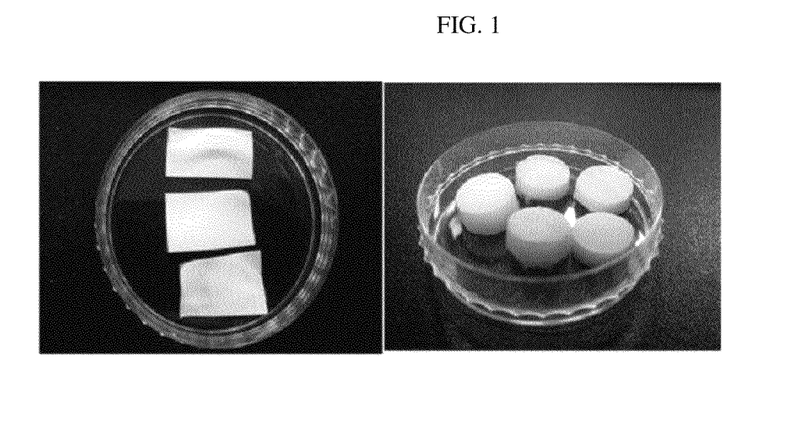
FIG. 1 shows a collagen membrane and a three-dimensional scaffold.
Figure 2:
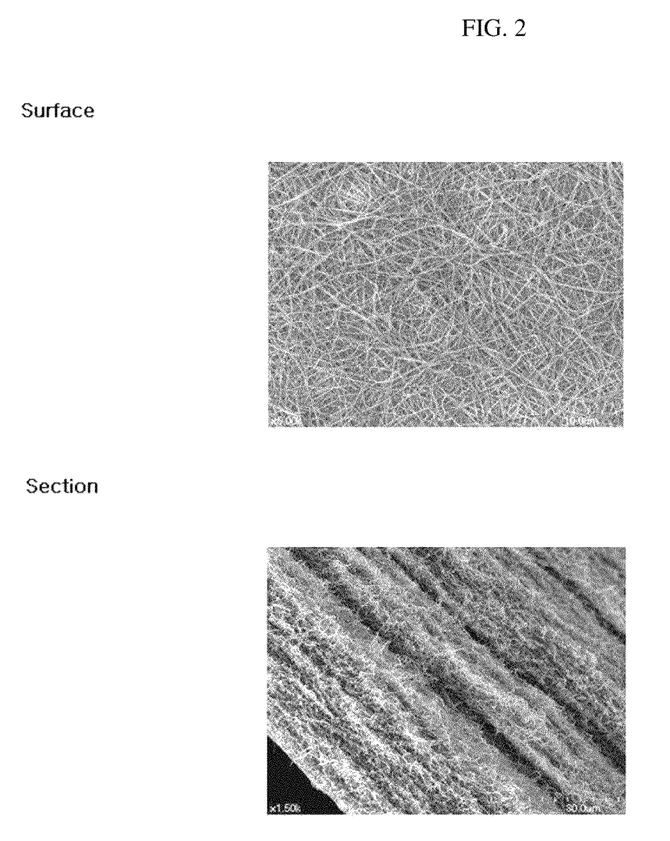
FIG. 2 is a set of scanning electron microscope (SEM) photographs showing the surface and cross-section of a collagen membrane.

In order to prepare a membrane, 8 ml of the concentrated collagen solution was poured in a 60-cm-diameter dish and mixed, and in order to prepare a three-dimensional scaffold, 1 ml of the collagen solution was poured in a 24-well plate for cell culture and mixed. Then, 1% glutaraldehyde or 1% glyceraldehydes was added to crosslink the collagen solution, and the crosslinked collagen was washed with distilled water and freeze-dried (see FIG. 1).

0.038 g of the prepared membrane having a size of 1×1 cm and a thickness of 250 μm fall was wet with 10 mg of the fusion peptide of SEQ ID NO: 24 in 100 μl of deionized water (DW), allowed to stand at 4° C. for 8 hours, washed with PBS, and freeze-dried. The collagen membrane having the peptide bound thereto was added to 10 ml of PBS and subjected to a peptide release test at 37° C.

After 7 days, 10 ml of the elution solvent added was completely removed, and then 10 ml of a fresh elution solvent was added to the collagen membrane which was then eluted at 37° C. for 4 weeks. After completion of the elution, the membrane was collected and the peptide content thereof was measured.

The elution test was performed for 4 weeks and the content of the peptide in the eluate was measured, and as a result, in Lot Nos. 1, 2 and 3, the peak of the peptide was not observed at the retention time of 13 minutes, but the peptide contents measured after completion of the elution were 9.2 mg, 9.43 mg and 9.68 mg (see Tables 2 and 3). This suggests that the peptide bound to the membrane was released into the eluate and that the peptide was stably bound to the membrane.

Method for Preparation of Sample Solution 0.038 g of the membrane having the peptide bound thereto was precisely weighed, and 5 ml of mobile phase solvent A was added thereto, followed by sonication for 1 hour. Next, 5 ml of mobile phase solvent B was added to and mixed with the membrane solution, and then the mixture was centrifuged at 4500 rpm for 30 minutes. 1 ml of the supernatant was taken and filtered through a 0.22 millipore filter to obtain a sample solution.

Method for Preparation of Standard Solution

A peptide standard was dried in a desiccator (silica gel) for 5 hours, and about 10 mg of the dried peptide was dissolved in mobile phase solvent A. 10 ml of the solution was used as a standard solution.

Test Method

10 μl of each of the sample solution and the standard solution was tested under the following operating conditions of liquid chromatography to measure the peak area $A_T$ of each of the sample solution and the standard solution.

Peptide amount (mg)=amount (mg) of peptide standard×$A_T/A_T$

The analysis conditions of liquid chromatography were as follows:

Instrument: analytical HPLC (Shimadzu, Japan);

Column: packed with C18-bonded silica gel having a size of 5 um (length: 250 mm, and inner diameter: 4.6 mm);

Mobile phase: 0.1% trifluoroacetic acid/DDW (solvent A), and 0.098% trifluoroacetic acid/acetonitrile (solvent B);

Detector: UV spectrophotometer (measurement wavelength: 230 nm);

Flow rate: 1 ml/min

Column temperature: constant temperature of 40° C.

TABLE 1

Gradient conditions

| Time (min) | B solvent composition (%) |
| --- | --- |
| 1 | 5 |
| 35 | 100 |
| 45 | 100 |
| 50 | 5 |
| 60 | 5 |

TABLE 2

Results of release of the peptide of SEQ ID NO: 24 from collagen membrane

| Lot No. | Days | Name | Ret. Time | Area | Height | mg |
| --- | --- | --- | --- | --- | --- | --- |
| 1 | 7 | RT13 | 0.000 | 0 | 0 | 0 |
|   | 14 | RT13 | 0.000 | 0 | 0 | 0 |
|   | 28 | RT13 | 0.000 | 0 | 0 | 0 |
| 2 | 7 | RT13 | 0.000 | 0 | 0 | 0 |
|   | 14 | RT13 | 0.000 | 0 | 0 | 0 |
|   | 28 | RT13 | 0.000 | 0 | 0 | 0 |
| 3 | 7 | RT13 | 0.000 | 0 | 0 | 0 |
|   | 14 | RT13 | 0.000 | 0 | 0 | 0 |
|   | 28 | RT13 | 0.000 | 0 | 0 | 0 |

TABLE 3

Content of the peptide of SEQ ID NO: 24 remaining on collagen membrane

| Lot No. | Name | Ret. Time | Area | Height | mg |
|---|---|---|---|---|---|
| 1 | RT13 | RT13 | 1276751 | 51132 | 9.20 |
| 2 | RT13 | RT13 | 1374499 | 51711 | 9.43 |
| 3 | RT13 | RT13 | 144963 | 56018 | 9.68 |

Example 3

Examination of In Vivo Stability of Fusion Peptide that Binds to Collagen and has the Ability to Regenerate Bone Tissue The peptide of SEQ ID NO: 24 labeled with FITC was bound to a collagen membrane in the same manner as described in Example 2. The collagen membrane was transplanted into the skull defect of a rabbit, and after 4 weeks, the membrane transplanted into the skull defect was observed by confocal microscopy (Olympus, Japan). Before and at days 1, 3, 7, 14, 21 and 28 after 10 mg of the peptide of SEQ ID NO: 24 labeled with FITC was transplanted into the rabbit skull defect, the blood was collected and whether the peptide was released into the systemic blood was measured using a fluorometer.

Figure 3:
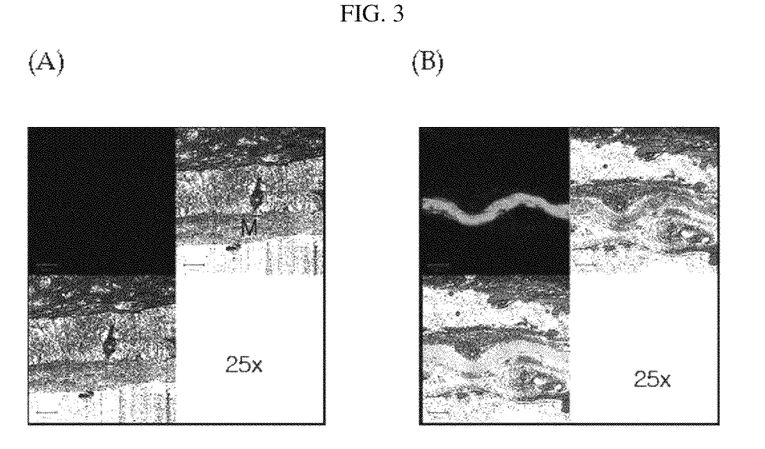
FIG. 3 is a set of confocal micrographs of collagen membranes.
Figure 4:
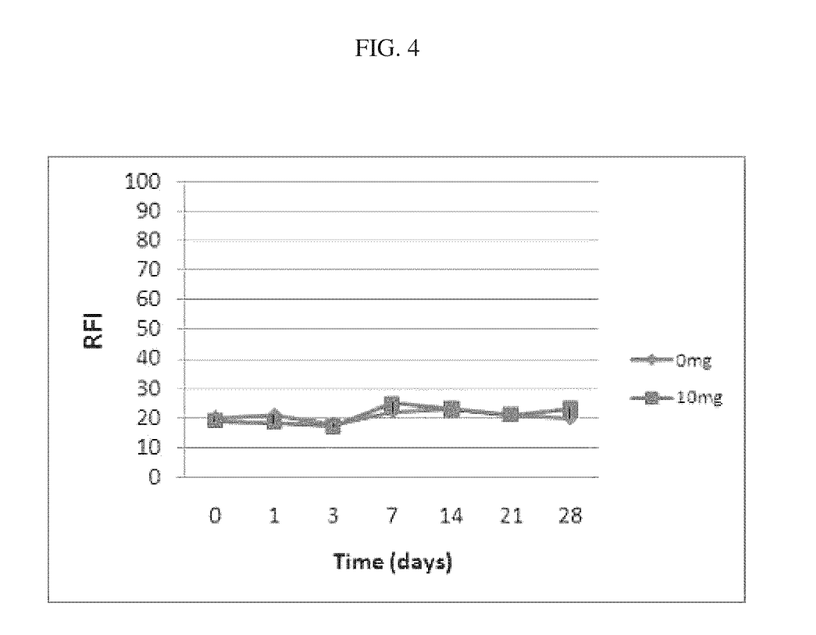
FIG. 4 shows the values obtained by transplanting a FITC-labeled collagen membrane into the circular skull defect of a rabbit, collecting the blood at varying points of time and measuring a peptide, released into the blood, using a fluorometer.

As a result, it was shown that the peptide was well fixed to the surface of the membrane transplanted into the skull and did not spread to the surrounding tissue (see FIG. 3). In addition, the RFI values for the membrane did not differ from the value before transplantation, suggesting that the peptide included in the membrane was not released into the blood, indicating that the peptide was well fixed to the collagen membrane (see FIG. 4).

Example 4

Examination of In Vivo Bone Regeneration Ability of Fusion Peptide that Binds to Collagen Membrane and has the Ability to Regenerate Bone Tissue Each of the peptides of SEQ ID NOS: 1, 9 and 24, prepared in Example 1, was bound to a collagen membrane according to the method of Example 2, and then transplanted into the circular skull defect of rabbits, and the bone regeneration ability was examined. Specifically, a circular bone defect having a diameter of 8 mm was formed in the skull of anesthetized rabbits (New Zealand white rabbits; species name: Cuniculus) and covered with the collagen membrane, and the periosteum and the skin were doubly sutured. At 4 weeks after the transplantation, the animal was sacrificed, and the collected sample was fixed in a formalin solution. The tissue was embedded to prepare a sample having a thickness of 20 μm. The prepared sample was stained with fuchsin and toluidine blue to prepare a nondem neralized sample. The prepared sample was observed with an optical microscope and photographed.

Figure 5:
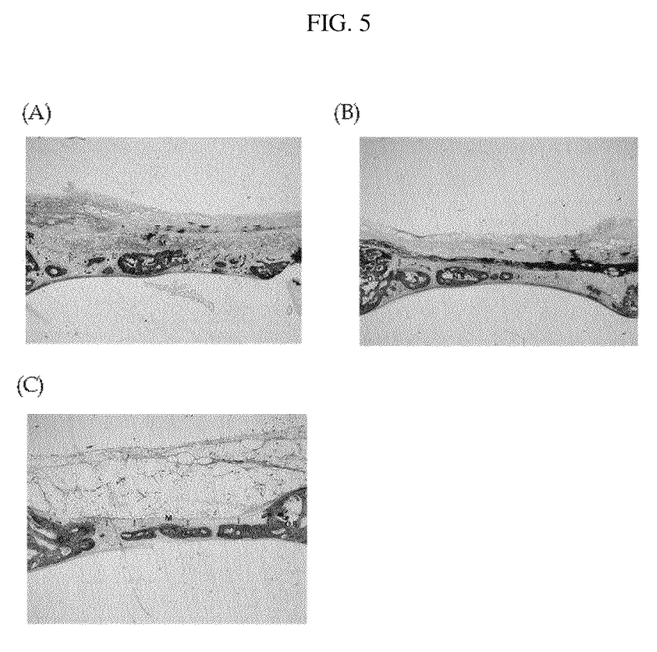
FIG. 5 is a set of photographs showing the degree of bone regeneration at 4 weeks after transplanting collagen membranes into the circular skull defects of rabbits.

The bone regeneration effect of the membrane including the fusion peptide that binds specifically to collagen and has the ability to regenerate bone tissue was examined, and as a result, the bone regeneration ability of the collagen membrane having the peptide of SEQ ID NO: 24 bound thereto was increased compared to that of the collagen membrane having the peptide of SEQ ID NO: 1 or 9 bound thereto, suggesting that the fusion peptide stably bound to collagen has an increased ability to regenerate bone tissue, because it stably resides in the transplanted site (see FIG. 5). Thus, it can be seen that the use of the membrane having bound thereto the fusion peptide, which binds specifically to collagen and has the ability to regenerate bone tissue, will show a significant effect on the regeneration of bone tissue.

Example 5

Preparation of Fusion Peptide that Binds Specifically to Collagen and has Antibacterial Activity In order to prepare a fusion peptide that binds specifically binds to collagen and has antibacterial activity, the peptide of SEQ ID NO: 1 (GLRSKSKKFRRPDIQYPDA) that binds to collagen and the peptide of SEQ ID NO: 26 (GKCSTR-GRKCCRRKK) that has antibacterial activity were synthesized. Using the synthesized peptides, an antibacterial fusion peptide (SEQ ID NO: 29) that binds specifically to collagen was synthesized in the same manner as described in Example 1.

```
SEQ ID NO: 29:
GLRSKSKKFRRPDIQYPDAGKCSTRGRKCCRRKK
```

Example 6

Examination of Antibacterial Activity of Fusion Peptide that Binds Specifically to Collagen Using each of the peptides of SEQ ID NOS: 1, 26 and 29, collagen membranes were prepared in the same manner as described in Example 2. Each of the prepared collagen membranes was allowed to stand in 10 ml of PBS for 1 hour and dried in air.

To evaluate the antibacterial activity of the peptides, an antibacterial test was performed according to the agar diffusion method. Specifically, E. coli cells were cultured in TSB (tryptic soy broth) medium until the absorbance at 620 nm reached 1, and then the cells were harvested and used in the test. The harvested cells were diluted with PBS, and $10^5$-$10^7$ bacterial cells per ml were plated on a TSA plate and incubated at 37° C. for 24 hours. On the plate having the incubated bacterial cells thereon, a collagen membrane having each of the peptides of SEQ ID NOS: 1, 26 and 29 bound thereto was placed and incubated for 3 days, and then the inhibition diameter against the bacterial cells was inhibited was measured.

Figure 6:
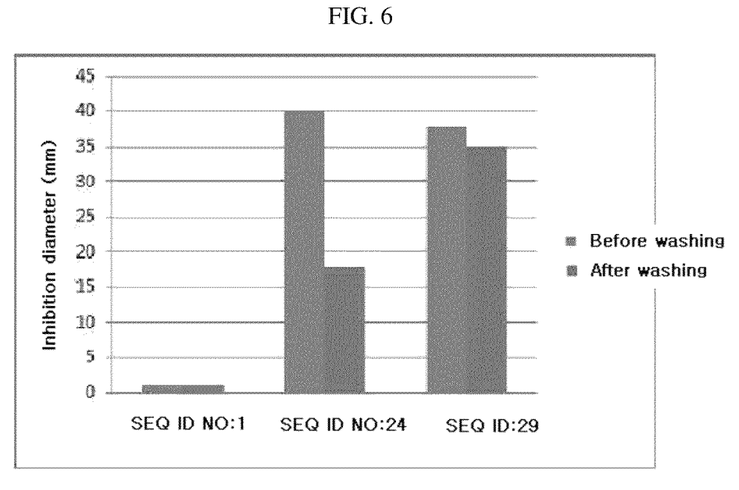
FIG. 6 shows the inhibition diameter of a collagen membrane against the growth of *E. coli*.

As a result, it could be seen that the collagen membrane having the peptide of SEQ ID NO: 1 bound thereto had no antibacterial activity before and after washing, and the collagen membrane having the peptide of SEQ ID NO: 26 bound thereto showed the highest antibacterial activity before washing, but the antibacterial activity thereof decreased by about 50% after washing. In addition, the collagen membrane having the peptide of SEQ ID NO: 29 bound thereto maintained its antibacterial activity after washing compared to before washing (see FIG. 6). This suggests that the fusion peptide of the collagen-binding peptide and the antibacterial peptide maintained its collagen-binding ability even after washing, and for this reason, the antibacterial activity thereof did not change.

Sequence List (Free Text)
Attach Electric File.

INDUSTRIAL APPLICABILITY

The present invention provides a collagen membrane having surface activity by a fusion peptide bound to the surface thereof. When the collagen membrane is transplanted in vivo, the retention time of the fusion peptide in a local region can increase, and the fusion peptide can promote the cell migration, proliferation and differentiation associated with bone tissue regeneration, thereby maximizing the ability to regenerate bone tissue. Thus, the collagen membrane contributes to the development of therapeutic technology for bone induction and regeneration. Also, the fusion peptide may be applied to other types of graft materials made of collagen. In addition, the collagen-binding peptide of the fusion peptide can also be bound to peptides having the effect of regenerating other tissues, and thus can be applied as a biomaterial for regeneration of other tissues such as the skin.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A fusion peptide having collagen-binding ability and antibacterial activity, the fusion peptide comprising a collagen-binding peptide having the amino acid sequence of SEQ ID NO: 1 linked to a peptide having the amino acid sequence of SEQ ID NO: 26.

2. The fusion peptide of claim 1, wherein the fusion peptide has the amino acid sequence set forth in SEQ ID NO: 29.

3. A collagen membrane having antibacterial activity, the collagen membrane comprising the fusion peptide of claim 1 or claim 2 fixed to the surface thereof.

* * * * *